US008439836B2

(12) United States Patent
Storm

(10) Patent No.: US 8,439,836 B2
(45) Date of Patent: May 14, 2013

(54) METHOD AND APPARATUS FOR MONITORING THE AUTONOMOUS NERVOUS SYSTEM OF A SEDATED PATIENT

(75) Inventor: Hanne Storm, Oslo (NO)

(73) Assignee: Med Storm Innovation AS, Oslo (NO)

( * ) Notice: Subject to any disclaimer, the term of this patent is extended or adjusted under 35 U.S.C. 154(b) by 1925 days.

(21) Appl. No.: 10/513,654

(22) PCT Filed: May 7, 2003

(86) PCT No.: PCT/NO03/00148
§ 371 (c)(1),
(2), (4) Date: Nov. 5, 2004

(87) PCT Pub. No.: WO03/094726
PCT Pub. Date: Nov. 20, 2003

(65) Prior Publication Data
US 2005/0229478 A1 Oct. 20, 2005
US 2009/0229171 A9 Sep. 17, 2009

(51) Int. Cl.
*A61B 5/00* (2006.01)
(52) U.S. Cl.
USPC .......................................................... 600/306
(58) Field of Classification Search .................. 600/306, 600/554, 557
See application file for complete search history.

(56) References Cited

U.S. PATENT DOCUMENTS

| 5,906,208 | A | 5/1999 | Ishikawa | |
|---|---|---|---|---|
| 6,757,558 | B2 * | 6/2004 | Lange et al. | 600/544 |
| 2001/0031916 | A1 | 10/2001 | Bennett et al. | |
| 2004/0193068 | A1 * | 9/2004 | Burton et al. | 600/544 |

FOREIGN PATENT DOCUMENTS

| SU | 1688844 | 11/1991 |
|---|---|---|
| WO | WO 85/00785 | 2/1985 |
| WO | WO 00/72751 | 12/2000 |
| WO | WO 02/100267 | * 12/2002 |

OTHER PUBLICATIONS

U.S. Appl. No. 10/731,816—Oath and Bib data sheet.*

* cited by examiner

*Primary Examiner* — Patricia Mallari
*Assistant Examiner* — Christian Jang
(74) *Attorney, Agent, or Firm* — Christian D. Abel

(57) ABSTRACT

The invention relates to a method and an apparatus for monitoring the autonomous nervous system of a sedated patient. According to the method, skin conductance is measured through a time interval. Average skin conductance values and the number of fluctuation peaks are in the interval are calculated and analyzed, and an indication is given of the state of pain/discomfort in the patient as well as the state of awakening in the patient. The invention is particularly applicable for use with anaesthetized or artificially ventilated patents, as separate output signals are automatically provided, indicating the need for analgesics and hypnotics, respectively.

16 Claims, 4 Drawing Sheets

METHOD AND APPARATUS FOR MONITORING THE AUTONOMOUS NERVOUS SYSTEM OF A SEDATED PATIENT

TECHNICAL FIELD

The invention relates in general to medical technology, and in particular to a method and an apparatus for monitoring the autonomous nervous system of a sedated patient. More specifically, the invention relates to a method and an apparatus for concurrently indicating the possible state of pain/discomfort and the possible state of awakening of a sedated patient, based on measurements of the patient's skin conductance.

BACKGROUND OF THE INVENTION

In the field of medical technology there is a problem in producing physical measurements representing the activity in an individual's autonomous nervous system, i.e. in the part of the nervous system, which is beyond the control of the will. Particularly, there is a special need to monitor the autonomous nervous system of a sedated, non-verbal patient, e.g. a patient in anaesthesia or an artificially ventilated patient, in order to detect if the patient needs more analgesics due to pain/discomfort stimuli or hypnotics because of awakening stimuli.

Analgesics are given to avoid pain/discomfort, and hypnotics are given to avoid awakening. Pain/discomfort can induce awakening and awakening rarely induce pain/discomfort. If hypnotics is given to a patient that feels pain/discomfort, the stress activation may be reduced, but the patient may still feel pain/discomfort. It is therefore a need for providing a monitoring system that can give information about if the stress activation found in sedated patients is due to pain/discomfort stimuli or awakening stimuli.

Both patients in anaesthesia and patients that are artificially ventilated are treated with analgesics and hypnotics. Currently, the stress activation of these patients is monitored by an increase in blood pressure and heart rate. Blood pressure and heart rate is influenced by many other factors than the need of analgesics or hypnotics, like blood circulatory changes found in heart disease, hypertension, lung disease, anaemia, blood loss and sepsis to name a few.

1-2% of the patients in anaesthesia feel pain during surgery. The development in medication in anaesthesia is to give both hypnotics and analgesics with very short half-life. Then it will be even more important to monitor the patient's need of analgesics and hypnotics.

Tests have shown that the skin's conductance changes as a time variable signal which, in addition to a basal, slowly varying value (the so-called basal level or the average conductance level through a certain interval), also has a component consisting of spontaneous waves or fluctuations, in which characteristics of these fluctuations, such as for example their frequency and amplitude, are factors which are correlated with the experience of pain in the target object (the patient). Measuring and analyzing characteristics of these fluctuations is a known method of providing information concerning the activity in the sympathetic nervous system, including the effect of pain.

RELATED BACKGROUND ART

WO 00/72751 A1 discloses a method and an apparatus for monitoring the autonomous nervous system of an individual. According to the method, a measurement signal is provided, expressing the conductance of at least one area of the individual's skin. The measured signal values are stored at discrete points of time in a time window. Further according to the method, an analysis of the measurement signal is performed in the time window, including calculating the amplitude and the number of fluctuation peaks in the conductance signal in said time window. From said characteristics of the peaks an output signal is established, indicating the state of pain in the individual.

This method provides an indication of pain, but no indication of awakening. When used for monitoring a sedated patient, the prior art method may provide an indication of lack of analgesics, but it does not provide an indication of lack of hypnotics due to awakening.

WO 85/00785 A1 discloses an apparatus for monitoring the attention or concentration of a person such as a long distance coach driver. Volar skin resistance is monitored, and if the resistance rises more than a predetermined amount, a stimulus, e.g. an audible tone in a headset may be emitted to alert the driver and to increase his concentration.

Although this simple way of monitoring of the skin resistance value may give an indication of the person's attention, it would not provide an indication, which is satisfactorily reliable for use when monitoring the awakening of a sedated patient. In particular, this prior art solution does not provide indications of pain/discomfort and awakening simultaneously.

SUMMARY OF THE INVENTION

An object of the present invention is to provide a method and an apparatus for monitoring the autonomous nervous system of a sedated patient, which indicates a state of pain/discomfort in the patient and which also provides an indication of awakening of the patient.

Another object of the invention is to provide such a method and apparatus, which relies on the measurement of skin conductance variations due to emotional sweating.

Still another object of the invention is to provide such a method and apparatus, which provides reliable output indications.

According to the invention, the above objects are achieved by the method as indicated in the appended claim 1 and by the apparatus as indicated in the appended claim 10

Further advantages and characteristics of the invention are indicated in the dependent claims.

Emotional sweating provides a more accurate and precise means of monitoring the need for hypnotics (after awakening stimuli) and analgesics (after pain/discomfort stimuli) than measurements of blood pressure and heart rate. As opposed to blood pressure and heart rate, the emotional sweating is not influenced by blood circulatory changes found in heart disease, hypertension, lung disease, anaemia, blood loss and sepsis, to name a few. Moreover, when measuring blood pressure and heart rate changes, health care staff is not able to know if the patient needs more analgesics or hypnotics.

BRIEF DESCRIPTION OF THE DRAWINGS

The apparatus and method according to the invention will now be described in more detail with reference to the attached drawings, in which.

DETAILED DESCRIPTION OF THE INVENTION

Figure 1:
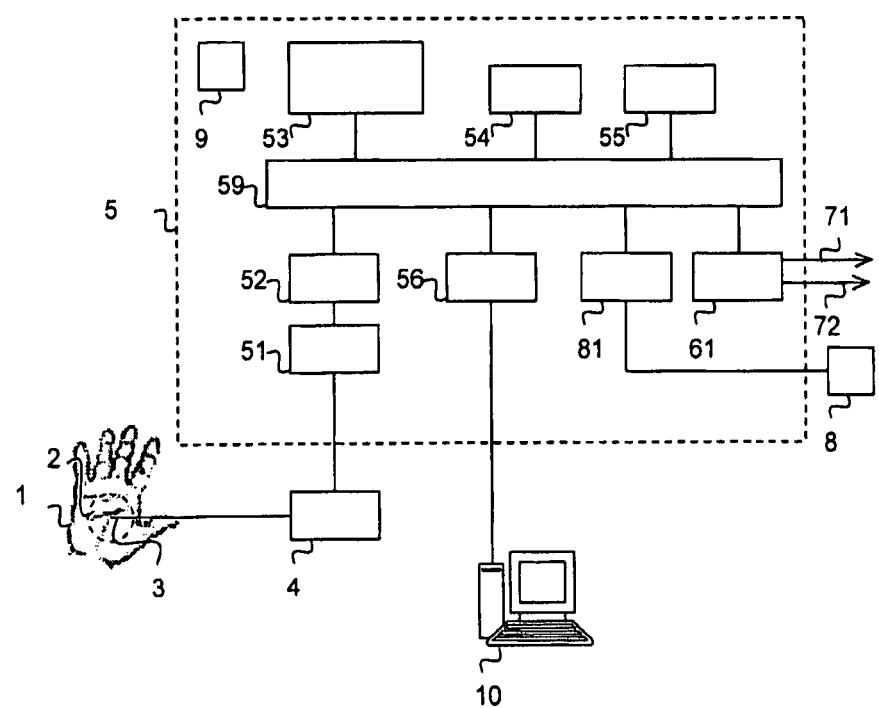
FIG. 1 is block diagram for an apparatus according to the invention.

FIG. 1 illustrates a block diagram for a preferred embodiment of an apparatus according to the invention. The apparatus is particularly arranged for the simultaneous detection of pain/discomfort reaction and awakening in a sedated patient. On an area 2 of the skin on a body part 1 of the patient, sensor means 3 are placed for measuring the skin's conductance. The body part 1 is preferably a hand or a foot, and the area 2 of the skin on the body part 1 is preferably the palmar side of the hand (in the palm of the hand) or the plantar side of the foot (under the sole of the foot). The sensor means 3 comprise contact electrodes where at least two electrodes are placed on the skin area 2. In a preferred embodiment the sensor means 3 consist of three electrodes: a signal electrode, a measuring electrode and a reference voltage electrode, which ensures a constant application of voltage over the stratum corneum (the surface layer of the skin) under the measuring electrode. The measuring electrode and the signal electrode are preferably placed on the skin area 2. The reference voltage electrode may also be placed on the skin area 2, but it is preferably placed in a nearby location, suitable for the measuring arrangement concerned.

In a preferred embodiment an alternating current is used for measuring the skin's conductance. The alternating current advantageously has a frequency in the range of up to 1000 Hz, corresponding to the area where the skin's conductance is approximately linear. A frequency should be selected which ensures that the measuring signal is influenced to the least possible extent by interference from, e.g., the mains frequency. In a preferred embodiment the frequency is 88 Hz. A signal generator, operating at the specified frequency, applies a signal current to the signal electrode.

In the case of alternating current the conductance is identical to the real part of the complex admittance, and therefore not necessarily identical with the inverse value of the resistance. An advantage of using alternating current instead of direct current in conductance measurement is that by this means one avoids the invidious effect on the measurements of the skin's electrical polarizing properties.

The resulting current through the measuring electrode is conveyed to a measurement converter 4. This comprises a current to voltage converter, which in a preferred embodiment is a transresistance amplifier, but in its simplest form may be a resistance, which converts the current from the measuring electrode to a voltage.

The measurement converter further comprises a decomposition circuit, preferably in the form of a synchronous rectifier, which decomposes the complex admittance in a real part (the conductance) and an imaginary part (the susceptance). However, it is sufficient if the decomposition circuit only comprises means for deriving the conductance. The synchronous rectifier multiplies the measured voltage with the voltage from the signal generator. The two signals are in-phase. After multiplication, the result is according to the cosine (2u) equation, where the result is a DC component and one component at 2u frequency. In the preferred embodiment, this becomes 176 Hz. In the preferred embodiment, this synchronous rectifier is realized as an analog circuit with the required accuracy.

The measurement converter 4 may also comprise amplifier and filter circuits. In the preferred embodiment the measurement converter contains low-pass filters, both at the input and at the output. The object of the input low-pass filter is to attenuate high-frequency noise, for instance coming from other medical equipments, and also to serve as anti-aliasing filter to prevent high frequency components from being received by subsequent circuits for time discretization. The output low-pass filter shall attenuate the 2u components that result from the multiplication operation in the synchronous rectifier so that only the signal near DC is used for further processing.

By means of the choice of components and design details, moreover, the measurement converter is designed with a view to obtaining high sensitivity and a low noise level.

The control unit 5 comprises a time discretization unit 51 for time discretization of the signal from the measurement converter. The time discretization takes place at a sampling rate, which may advantageously be in the order of 20 to 200 samplings per second. The control unit further comprises an analog-digital converter 52, which converts measurement data to digital form. The choice of circuits for time discretization and analog-digital conversion implies technical decisions suitable for a person skilled in the art. In the preferred embodiment, time discretization is done in an integrated circuit, which combines oversampling, filtering and discretization.

The control unit may advantageously comprise additional analog and possibly also digital inputs (not illustrated), in addition to the input from the measurement converter 4. In this case the control unit 5 can either be equipped with a plurality of analog-digital converters 52, or it can employ various multiplexing techniques well-known to those skilled in the art in order to increase the number of analog inputs. These additional analog inputs may, for example, be arranged for additional electrodermal measurements, or for other physiological measurements which may advantageously be performed simultaneously or parallel with the electrodermal measurement, such as temperature, pulse, ECG, respiratory measurements, oxygen saturation measurements in the blood, or EEG (bispectral index).

The control unit 5 also comprises a processing unit 53 for processing the digitized measurement data, storage means in the form of at least one store for storing data and programs, illustrated as a non-volatile memory 54 and a random access memory 55. The control unit 5 further comprises an interface circuit 61, which provides output signals 71, 72. Preferably, the control unit 5 further comprises a further interface circuit 81, which is further connected to display unit 8. The control unit 5 may also advantageously comprise a communication port 56 for digital communication with an external unit, such as a personal computer 10. Such communication is well-suited for loading or altering the program which is kept stored in the memory 54, 55 in the control unit, or for adding or altering other data which are kept stored in the memory 54, 55 in the control unit. Such communication is also well suited for read-out of data from the memory 54, 55 in the apparatus, thus enabling them to be transferred to the external computer 10 for further, subsequent analysis or storage. A communication port 56 in the control unit will be advantageously designed in accordance with requirements for equipment safety for patients, as described in more detail below.

In a preferred embodiment the non-volatile memory 54 comprises a read-only storage in the form of programmable ROM circuits, containing at least a program code and permanent data, and the random access memory 55 comprises a read and write storage in the form of RAM circuits, for storage of measurement data and other provisional data.

The control unit 5 also comprises an oscillator (not shown), which delivers a clock signal for controlling the processing unit 53. The processing unit 53 also contains timing means (not shown) in order to provide an expression of the current time, for use in the analysis of the measurements. Such timing means are well-known to those skilled in the art, and are often included in micro controllers or processor systems which the skilled person will find suitable for use with the present invention.

The control unit 5 may be realized as a microprocessor-based unit with connected input, output, memory and other peripheral circuits, or it may be realized as a micro controller unit where some or all of the connected circuits are integrated. The time discretization unit 51 and/or analog-digital converter 52 may also be included in such a unit. The choice of a suitable form of control unit 5 involves decisions, which are suitable for a person skilled in the art.

An alternative solution is to realize the control unit as a digital signal processor (DSP).

The control unit 5 is arranged to read time-discrete and quantized measurements for the skin conductance from the measurement converter 4, preferably by means of an executable program code, which is stored in the non-volatile memory 54 and which is executed by the processing unit 53. It is further arranged to enable measurements to be stored in the read and write memory 55. By means of the program code, the control unit 5 is further arranged to analyze the measurements in real time, i.e. simultaneously or parallel with the performance of the measurements. In this context, simultaneously or parallel should be understood to mean simultaneously or parallel for practical purposes, viewed in connection with the time constants which are in the nature of the measurements. This means that input, storage and analysis can be undertaken in separate time intervals, but in this case these time intervals, and the time between them, are so short that the individual actions appear to occur concurrently.

The control unit 5 is further arranged to identify an average value for the discrete, quantized measuring signal during a time interval, by means of a program code portion which is stored in the non-volatile memory 54 and which is executed by the processing unit 53.

The control unit 5 is further arranged to identify the fluctuations in the time-discrete, quantized measuring signal, by means of a program code portion which is stored in the non-volatile memory 54 and which is executed by the processing unit 53.

The control unit 5 is further arranged to count or calculate the number of fluctuation peaks in the time-discrete, quantized measuring signal during a time interval, by means of a program code portion which is stored in the non-volatile memory 54 and which is executed by the processing unit 53.

The processing unit 53, the memories 54, 55, the analog/digital converter 52, the communication port 56, the interface circuit 81 and the interface circuit 61 are all connected to a bus unit 59. The detailed construction of such bus architecture for the design of a microprocessor-based instrument is regarded as well-known for a person skilled in the art.

The interface circuit 61 is a digital port circuit, which derives digital output signals 71, 72 from the processing unit 53 via the bus unit 59 when the interface circuit 61 is addressed by the program code executed by the processing unit 53.

The first digital output signal 71 indicates that the analysis of the skin conductance measurement has detected that a state of pain/discomfort has occurred in the patient. The second output signal 72 indicates that a state of awakening has occurred in the patient.

In a special application of the invention the warning signals 71, 72 or another signal derived from the processing means in the analysis of the skin conductance measurements may be used to control an automatic administration of a medication to the patient. Particularly, the administration of an analgesic medication may be controlled by the first signal 71 indicating pain/discomfort, and the administration of a sleep-inducing medication or hypnotic may be controlled by the second signal 72 indicating awakening. Each of the signals may be used, for example, to control a device for intravenous supply of medication. In this case the invention will form part of a feedback loop for control of the activity in the patient's autonomous nervous system.

In a preferred embodiment the display means 8 consist of a screen for graphic visualization of the conductance signal, and a digital display for displaying the frequency and amplitude of the measured signal fluctuations. The display units are preferably of a type whose power consumption is low, such as an LCD screen and LCD display. The display means may be separate or integrated in one and the same unit.

The apparatus further comprises a power supply unit 9 for supplying operating power to the various parts of the apparatus. The power supply may be a battery or a mains supply of a known type.

The apparatus may advantageously be adapted to suit the requirements regarding hospital equipment, which ensures patient safety. Such safety requirements are relatively easy to fulfill if the apparatus is battery-operated. If, on the other hand, the apparatus is mains operated, the power supply shall meet special requirements, or requirements are made regarding a galvanic partition between parts of the apparatus (for example, battery operated), which are safe for the patient and parts of the apparatus, which are unsafe for the patient. If the apparatus has to be connected to external equipment, which is mains operated and unsafe for the patient, the connection between the apparatus, which is safe for the patient and the unsafe external equipment requires to be galvanically separated. Galvanic separation of this kind can advantageously be achieved by means of an optical partition. Safety requirements for equipment close to the patient and solutions for fulfilling such requirements in an apparatus like that in the present invention are well-known to those skilled in the art.

Figure 2:
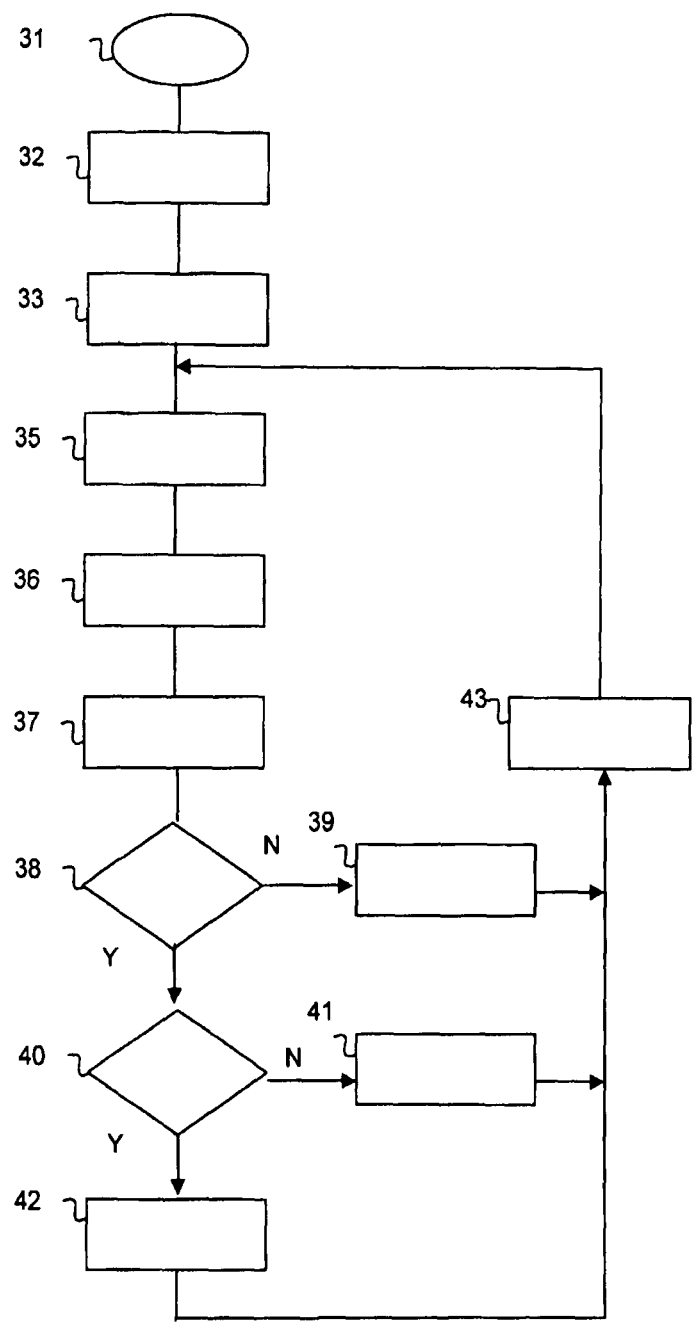
FIG. 2 is a flow chart illustrating a method according to the invention.

FIG. 2 illustrates a flow chart for a method for controlling a warning signal in an apparatus for monitoring the autonomous nervous system of a sedated patient, and especially for detecting pain/discomfort and awakening.

The method starts at reference 31.

The first two process steps 32 and 33 are initial steps, establishing initial values for use in the remaining, repeated process steps.

In the first step 32, a skin conductance signal or EDR (electrodermal response) signal is measured, time-quantized and converted to digital form using the equipment described with reference to FIG. 1. An initial time-series of a certain duration, typically a period of 20 seconds, containing skin conductance data, is acquired during this step. With a sampling rate of 20-200 samples per second, the time-series may contain 400-4000 samples.

This time-series is then analyzed. In step 33, an average conductance level or basal level through the initial time-series is calculated. This initial average conductance value is stored and used as the first "previous value" during the first execution of the comparison step 40 below.

In step 35, a skin conductance signal is again measured, time-quantized and converted to digital form using the equipment described with reference to FIG. 1. A time-series of a certain duration, typically a period of 20 seconds, containing skin conductance data, is acquired during this step.

This time-series is then analyzed. In step 36, an average conductance level or basal level through the current time-series is calculated. This initial average conductance value is stored and used as the current conductance average value during the execution of the comparison step 40 below.

In step 37, the number of fluctuation peaks in the conductance signal through the current time-series is calculated. This is performed by detecting local peaks or local maximum values and/or by detecting local valleys or local minimum values. Although the following detailed description refers to detecting peaks, the skilled person will realize that detecting valleys may be performed in an analogous way.

The existence of a peak is established if the derivative of the signal changes sign through a small period in the interval. The derivative of the signal is calculated as the difference between two subsequent sample values. In addition, it is possible to use a simple digital filter that needs to see two or more subsequent sign changes before the sign change is accepted.

In the calculation step 37 it may be necessary to establish additional criteria for when a peak should be considered as valid. In their simplest form such criteria may be based on the fact that the signal, in addition to the sign change of the derivative, has to exceed an absolute limit in order to be able to be considered a peak. A recommended, such limit value for the conductance is 0.02 µS.

Alternatively or in addition, it is an advantage to base the criteria on the fact that the signal actually has formed a peak that has lasted a certain time. The criteria may also be based on the fact that the increase in the skin conductance signal value as a function of time must remain below a certain limit, typically 20 µS/s, if the maximum value is to be considered valid.

Another possible condition for establishing a valid peak, is that the absolute value of the change in the conductance signal from a local peak to the following local valley exceeds a predetermined value, such as 0.02 µS.

Also, a maximum value appearing at the border of the interval, i.e. the starting point or ending point of the interval, should preferably not be regarded as a valid peak.

The object is thereby achieved that artifacts, which can occur in error situations such as, e.g., electrodes working loose from the skin, or other sources of noise or disturbances, does not lead to the erroneously detection of peaks.

The number of peaks calculated in step 37 is stored and used as the current number of peaks during the execution of the comparison step 38 below.

The conductance average calculating step 36 and the peak counting step 37 could alternatively be performed in reverse order, or concurrently, if desired.

The purpose of the following steps 38-42 is to realize the following functions:

If the number of peaks is above a certain limit, but the average conductance level is unchanged, then pain/discomfort is detected, output signal 71 is activated and output signal 72, if previously activated, is reset.

If the number of peaks is above said limit and the average conductance level is increasing, then a state of awakening is detected, output signal 72 is activated and output signal 71, if previously activated, is reset.

If neither of the above conditions is achieved, then output signal 71 or 72, if previously activated, is reset.

In the comparison step 38, the current calculated number of peaks is compared with a preset limit value. The Applicant's tests have shown that a suitable limit value is 0.1 peaks per second, i.e. 2 peaks per 20 seconds. Other values could possible be determined from clinical tests, in order to further optimize the performance and reliability of the output indications.

If the current number of peaks is equal to or higher than the preset limit value (output denoted Y), the process continues to the decision step 40. If on the other hand the current number of peaks is smaller than the preset limit value (output denoted N), the process is continued at step 39.

In step 39, both output signals 71 or 72 are reset, if any of them were previously activated.

In comparison step 40, the current average conductance value is compared with the previous average conductance value. If the current average conductance value is smaller than or equal to the previous average conductance value (output denoted N), the state of pain/discomfort should be indicated, and the process continues to step 41. If on the other hand the current average conductance value is larger (output denoted Y), the state of awakening should be indicated, and the process continues to step 42.

In step 41, the state of pain/discomfort is indicated. The processing unit 53 activates the first output signal 71, indicating a pain/discomfort state, via the interface circuit 61, and a pain/discomfort message is indicated on the display unit 8 by the use of the interface circuit 81. If the second output signal 72 is previously activated, it is reset. The process is then continued at the updating step 43.

In step 42, the state of awakening is indicated. The processing unit 53 activates the second output signal 72, indicating an awakening state, via the interface circuit 61, and an awakening message is indicated on the display unit 8 by the use of the interface circuit 81. If the first output signal 71 is previously activated, it is reset. The process is then continued at the updating step 43.

In the updating step 43, the current average conductance value is stored as the previous average conductance value. The process is then repeated from step 35.

The process may be interrupted or terminated by an operating device (not shown) or by a command input from the communication port 56.

A first improvement to the method illustrated in FIG. 2 will be described in the following:

In the comparison step 38 in FIG. 2, the current calculated number of peaks is compared with a preset limit value. Even more reliable results may be achieved for the pain/discomfort and awakening indications if this comparison is also dependent on the condition that the current number of peaks is larger than the previous number of peaks.

In order to perform this extended comparison, an additional step 34 should be performed subsequent to step 33, wherein the number of fluctuation peaks in the conductance signal through the initial period is calculated. This calculation is performed in the same way as described with reference to step 37. The initial number of peaks is stored and used as the "previous number of peaks" in the first execution of the extended comparison step 38.

Further, the comparison step 38 should be modified. In the modified comparison step 38, the current number of peaks is compared with the preset limit value and with the previous number of peaks. If the current number of peaks is larger than both the limit value and the previous number of peaks, the process continues to the comparison step 40. If on the other hand the number of peaks is equal to or less than the limit value or the previous number of peaks, or both, the process continues to step 39.

The updating step 43 should also be modified. In the modified updating step 43, the current number of peaks is stored as the previous number of peaks. In addition, the current average conductance value is stored as the previous average conductance value.

A second improvement to the embodiment illustrated in FIG. 2 will be described in the following:

In the embodiment in FIG. 2, a time-series is first acquired and subsequently analyzed. As an advantageous alternative, data acquisition and analysis are performed as separate, independent processes, concurrently executed by the processing unit 53.

A data acquisition process is then performed, which virtually continuously updates a portion of the memory 55 with the latest e.g. 20 seconds of skin conductance signal values.

An analysis process is initiated e.g. every 1 second. This process will analyze the latest e.g. 20 seconds of skin conductance data, acquired by the concurrently executed data acquisition process. All the process steps 35-43 are performed by the analysis process, while the initial process steps 32 and 33 are performed in advance, as initial steps.

This solution leads to an even faster and more reliable indication of pain/discomfort and awakening, compared to the simpler method described with reference to FIG. 2.

Figure 3A:
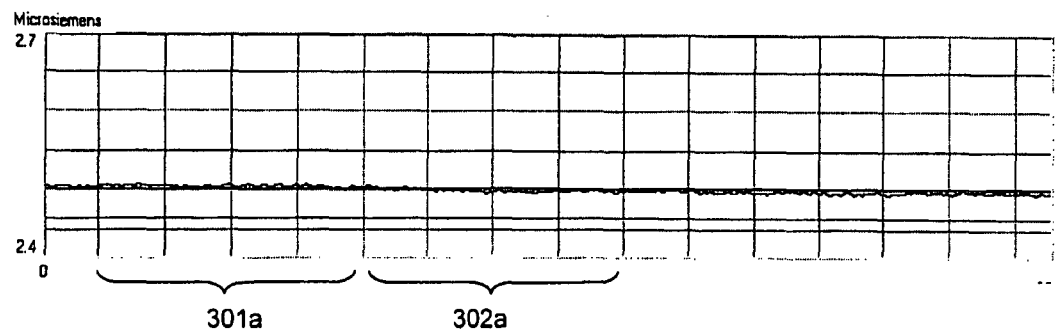
FIGS. 3a-c are three graphs, each illustrating a time-series of skin conductance measurements of a sedated patient, which is exposed to neither awakening stimuli nor pain/discomfort stimuli.
Figure 3B:
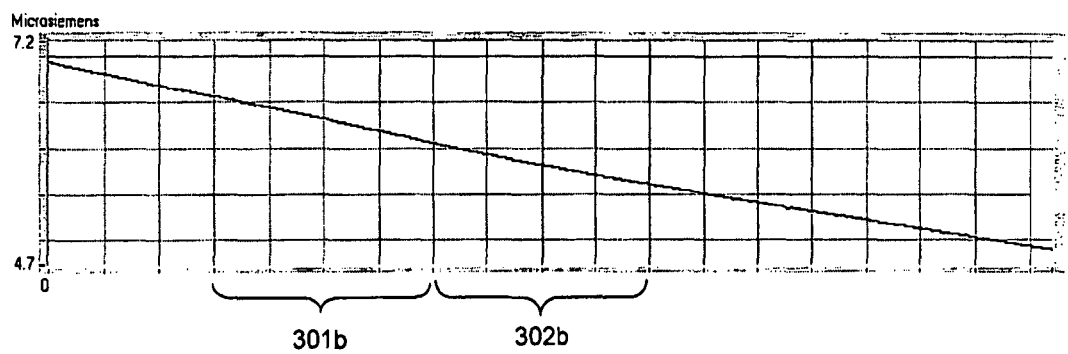
Figure 3C:
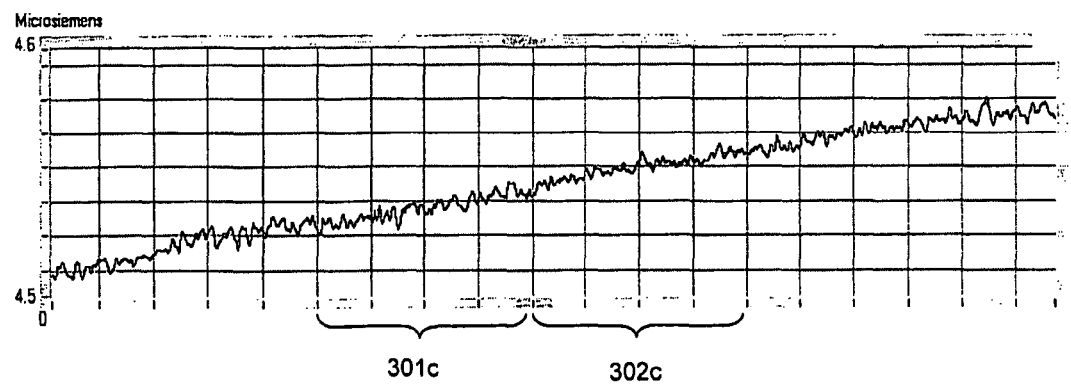

FIGS. 3a-c are three graphs, each illustrating a time-series of a skin conductance measurement signal (vertically) vs. time (horizontally) of a sedated patient, which is exposed to neither awakening stimuli nor pain/discomfort stimuli, FIG. 3a is a graph illustrating a skin conductance signal which is essentially steady.

A first time interval of about 20 seconds is indicated by 301a, and a second time interval of about 20 seconds is indicated by 302a.

Assume that the method according to the embodiment described with reference to FIG. 2 is applied to this signal, with the initial time-series corresponding to the time interval indicated by 301a, and the next time-series corresponding to the time interval indicated by 302a. The preset limit value is 2 peaks per 20 seconds. In the second time interval 302a the number of peaks will be calculated as zero. Then the current number of peaks will be less than the preset limit value. Consequently, the process continues to step 39, i.e. the pain/discomfort state signal and the awakening signal are both reset. The monitoring process will then be repeated, based on the time interval 302a as the previous time interval and a subsequent time interval (not illustrated) as the current time interval.

FIG. 3b is a graph illustrating a time-series of skin conductance measurements of a patient whose skin conductance is steadily decreasing.

A first time interval of about 20 seconds is indicated by 301b, and a second time interval of about 20 seconds is indicated by 302b.

Assume now that the method according to the embodiment described with reference to FIG. 2 is applied to this signal, with the initial time-series corresponding to the time interval indicated by 301b, and the next time-series corresponding to the time interval indicated by 302b. In the second time interval 302b the number of peaks will be calculated as 0. Then the number of peaks is recognized as below the preset limit of 2 per 20 seconds. Then the current number of peaks will be less than the preset limit value. Consequently, the process continues to step 39, i.e. the pain/discomfort state signal and the awakening signal are both reset. The monitoring process will then be repeated, based on the time interval 302b as the previous time interval and a subsequent time interval (not illustrated) as the current time interval.

FIG. 3c is a graph illustrating a time-series of skin conductance measurements of a patient whose skin conductance is steadily increasing.

A first time interval of about 20 seconds is indicated by 301c, and a second time interval of about 20 seconds is indicated by 302c.

Assume now that the method according to the embodiment described with reference to FIG. 2 is applied to this signal, with the initial time-series corresponding to the time interval indicated by 301c, and the next time-series corresponding to the time interval indicated by 302c.

The apparent fluctuations in the signal are due to noise with a relatively low magnitude (less than 0.02 µS). Provided that step 37 is implemented with the additional condition that the absolute value of the change in the conductance signal from a local peak to the following local valley should exceed the predetermined value 0.02 µS in order to consider a peak as valid, the apparent peaks will not be considered as valid peaks.

In the second time interval 302c the number of peaks will thus be calculated as 0. Then the number of peaks is recognized as below the preset limit value of 2 per 20 seconds. Then the current number of peaks will be less than the preset limit value. Consequently, the process continues to step 39, i.e. the pain/discomfort state signal and the awakening signal are both reset. The monitoring process will then be repeated.

Figure 4:
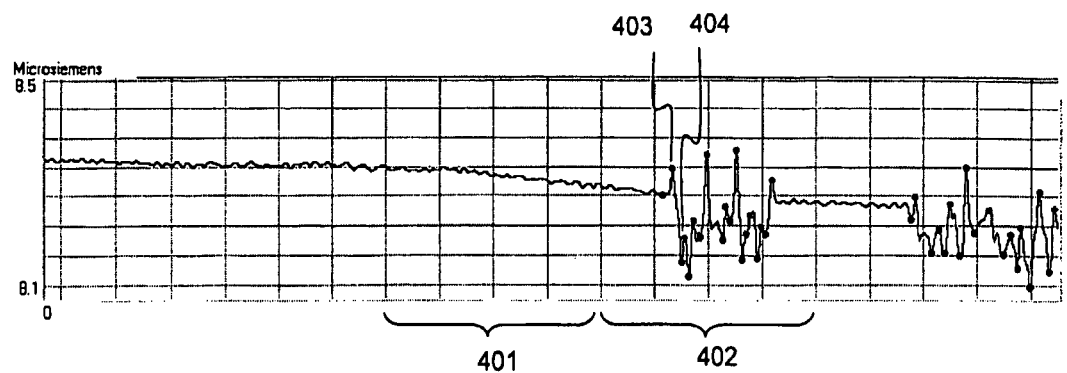
FIG. 4 is a graph illustrating a time-series of skin conductance measurements of a sedated patient which is exposed to pain/discomfort stimuli.

FIG. 4 is a graph illustrating a time-series of skin conductance measurements of a sedated patient, which is exposed to pain/discomfort stimuli.

A first time interval of about 20 seconds is indicated by 401, and a second time interval of about 20 seconds is indicated by 402. Two subsequent peaks out of several peaks in the skin conductance signal are indicated by 403 and 404.

Assume now that the method according to the embodiment described with reference to FIG. 2 is applied to this signal, with the initial time-series corresponding to the time interval indicated by 401, and the next time-series corresponding to the time interval indicated by 402. In the second time interval 402 the number of peaks will be calculated as 10. Then the number of peaks is recognized as equal to or above the preset limit. Consequently, the comparison step 40 will be executed.

Further, the average skin conductance value through the first time interval 401 will be calculated as about 8.3 microsiemens, and the average skin conductance value through the second time interval 402 will be calculated as about 8.2 microsiemens.

Then no increase in the average conductance value will be recognized in the comparison step 40. Thus, step 41 is entered, which means that the first output signal 71 is activated, and a state of pain/discomfort in the patient is indicated.

Then the process continues to step 43, i.e. the monitoring process is repeated, based on the time interval 402 as the previous time interval and a subsequent time interval (not illustrated) as the current time interval.

Figure 5:
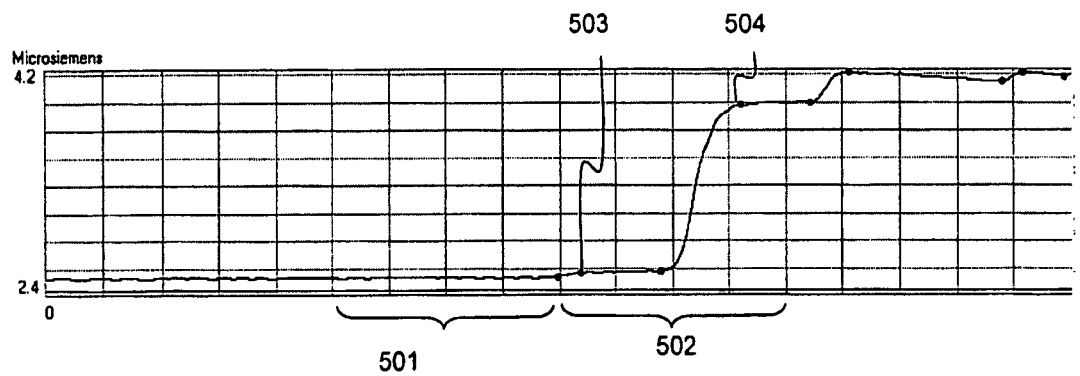
FIG. 5 is a graph illustrating a time-series of skin conductance measurements of a sedated patient which is exposed to awakening stimuli.

FIG. 5 is a graph illustrating a time-series of skin conductance measurements of a sedated patient, which is exposed to awakening stimuli.

A first time interval of about 20 seconds is indicated by 501, and a second time interval of about 20 seconds is indicated by 502. Two peaks in the skin conductance signals are indicated by 503 and 504.

Assume now that the method according to the embodiment described with reference to FIG. 2 is applied to this signal, with the initial time-series corresponding to the first time interval indicated by 501, and the next time-series corresponding to the second time interval indicated by 502. In the second time interval 502 the number of peaks will be calculated as 2. In the comparison step 38, the number of peaks is recognized as equal to or above the preset limit. Consequently, the comparison step 40 will be executed.

The average skin conductance value through the first time interval 501 will be calculated as about 2.4 microsiemens, and the average skin conductance value through the second time interval 502 will be calculated as about 3 microsiemens.

Consequently, an increase in the average conductance value is recognized in the comparison step 40. Thus, step 42 is executed and the second output signal 72 is activated, which means that a state of awakening in the patient is indicated. Then the process continues to step 43, i.e. the monitoring process is repeated, based on the time interval 502 as the previous time interval and a subsequent time interval (not illustrated) as the current time interval.

The above description and drawings present a specific embodiment of the invention, with the addition of some alternatives. For a person skilled in the art, however, it will be obvious that other, alternative embodiments exist which are within the scope of the present invention. For instance, the skin conductance signal may be measured using a DC method instead of the specifically described AC method. The use of skin resistance instead of skin conductance as the measurement signal will of course lead to equivalent results, if the inverse nature of these variables is taken into account. Although the detection of peaks are specified in the detailed description, the skilled person will realize that the same result will appear if valleys or minimum points are detected in a similar way.

Moreover, when a patient is exposed to induction of anesthesia, the number of peaks will decrease together with a decrease in average conductance level.

The inventive concept is thus not limited to the exemplary embodiments described above. Rather, the scope of the invention is set forth in the following patent claims.

The invention claimed is:

1. Method for monitoring the autonomous nervous system of a sedated patient, the method being performed by a control unit in an apparatus, comprising
   providing, from a measurement equipment, a skin conductance signal measured at an area of the patient's skin,
   calculating, by the control unit, characteristics of said skin conductance signal,
   establishing, by the control unit, a first output signal indicating the state of pain/discomfort in the patient, based on said characteristics of said skin conductance signal, wherein said characteristics comprise the average value of the skin conductance signal through a first time interval and the average value of the skin conductance signal through a second time interval, and the number of fluctuation peaks or valleys of the skin conductance signal through said second time interval, and
   establishing, by the control unit, a second output signal indicating the state of awakening in the patient, based on said characteristics of said skin conductance signal, said establishing step including
   comparing the number of fluctuation peaks or valleys through said second time interval with a limit value,
   and if the number of peaks or valleys is higher than the limit value, comparing the average conductance value through the second interval with the average conductance value through the first interval,
   and if the second average conductance value is the larger, establishing the second output signal as indicating the state of awakening in the patient.

2. Method according to claim 1,
   wherein said step of establishing the first output signal comprises
   comparing the number of fluctuation peaks or valleys through said second time interval with a limit value,
   and if the number of peaks or valleys is higher than the limit value,
   comparing the average conductance value through the second interval with the average conductance value through the first interval,
   and if the second average conductance value is not the larger,
   establishing the first output signal as indicating the state of pain/discomfort in the patient.

3. Method according to one of the claims 1-2,
   wherein the first and second intervals have equal duration.

4. Method according to claim 3,
   wherein the start point of the second interval is 0.5 to 5 seconds subsequent to the start point of the first interval.

5. Method according to claim 4,
   wherein the start point of the second interval is 1 second subsequent to the start point of the first interval.

6. Method according to one of the claims 1-3,
   wherein the start point of the second interval coincides with the end point of the first interval.

7. Method according to one of the claims 1-2, further comprising the step of supplying medication to the patient, controlled by the first output signal or the second output signal.

8. Method according to one of the claims 1-2, further comprising the step of supplying medication to the patient, controlled by the first output signal and the second output signal.

9. Apparatus for monitoring the autonomous nervous system of a sedated patient, comprising
   measurement equipment, providing a skin conductance signal measured at an area of the patient's skin,
   a data storage for storing the measured signal values at discrete points of time,
   a control unit arranged for
      reading the skin conductance signal,
      calculating characteristics of said skin conductance signal,
      establishing a first output signal indicating the state of pain/discomfort in the patient, based on said characteristics of said skin conductance signal,
   said characteristics comprising the average value of the skin conductance signal through a first time interval and the average value of the skin conductance signal through a second time interval, and the number of fluctuation peaks or valleys of the skin conductance signal through said second time interval, and
      establishing a second output signal indicating the state of awakening in the patient, based on said characteristics of said skin conductance signal, by performing the steps of
      comparing the number of fluctuation peaks or valleys through said second time interval with a limit value, and if the number of peaks or valleys is higher than the limit value,
comparing the average conductance value through the second interval with the average conductance value through the first interval,
and if the second average conductance value is the larger, establishing the second output signal as indicating the state of awakening in the patient.

10. Apparatus according to claim 9,
wherein the control unit is arranged to establish the first output signal by performing the steps of
comparing the number of fluctuation peaks or valleys through said second time interval with a limit value,
and if the number of peaks or valleys is higher than the limit value,
comparing the average conductance value through the second interval with the average conductance value through the first interval,
and if the second average conductance value is not the larger,
establishing the first output signal as indicating the state of pain/discomfort in the patient.

11. Apparatus according to one of the claims 9-10,
wherein the first and second intervals have equal duration.

12. Apparatus according to claim 11,
wherein the start point of the second interval is 0.5 to 5 seconds subsequent to the start point of the first interval.

13. Apparatus according to claim 12,
wherein the start point of the second interval is 1 second subsequent to the start point of the first interval.

14. Apparatus according to claim 11, wherein the start point of the second interval coincides with the end point of the first interval.

15. Apparatus according to one of the claims 9-10,
further comprising a device for supply of medication to the patient, controlled by the first output signal or the second output signal.

16. Apparatus according to one of the claims 9-10, further comprising a device for supply of medication to the patient, controlled by the first output signal and the second output signal.

* * * * *